(12) United States Patent
Lee et al.

(10) Patent No.: US 12,339,228 B2
(45) Date of Patent: Jun. 24, 2025

(54) NANOPARTICLES FOR SENSING PHOSPHATE, METHOD FOR MANUFACTURING THE SAME, AND MEMBRANE FOR SENSING PHOSPHATE INCLUDING THE SAME

(71) Applicants: Electronics and Telecommunications Research Institute, Daejeon (KR); The Industry & Academic Cooperation in Chungnam National University (IAC), Daejeon (KR)

(72) Inventors: Hyung-Kun Lee, Daejeon (KR); Jungseok Heo, Daejeon (KR); Do Yeob Kim, Daejeon (KR); Donggyu Kim, Daejeon (KR); Young Il Kim, Daejeon (KR); Bongjin Jeong, Daejeon (KR)

(73) Assignees: ELECTRIC AND TELECOMMUNICATIONS RESEARCH INSTITUTE, Daejeon (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 539 days.

(21) Appl. No.: 17/861,910

(22) Filed: Jul. 11, 2022

(65) Prior Publication Data
US 2023/0228680 A1    Jul. 20, 2023

(30) Foreign Application Priority Data
Jan. 19, 2022   (KR) .................. 10-2022-0007806

(51) Int. Cl.
*G01N 21/64* (2006.01)
*B01L 3/00* (2006.01)
*G01N 33/18* (2006.01)

(52) U.S. Cl.
CPC ............ *G01N 21/64* (2013.01); *B01L 3/5023* (2013.01); *G01N 33/18* (2013.01); *B01L 2300/069* (2013.01); *G01N 2021/6432* (2013.01)

(58) Field of Classification Search
CPC .... G01N 21/64; G01N 12/6408; G01N 33/18; G01N 33/54346; G01N 33/54366;
(Continued)

(56) References Cited

U.S. PATENT DOCUMENTS

| 7,416,703 B2 | 8/2008 | Murray et al. |
| 8,288,171 B2 | 10/2012 | Song et al. |

(Continued)

FOREIGN PATENT DOCUMENTS

| KR | 10-1628266 B1 | 6/2016 |
| WO | 2020/009016 | 1/2020 |

OTHER PUBLICATIONS

Tan et al: "Superhydrophobic PVDF/micro fibrillated cellulose membrane for membrane distillation crystallization of struvite", Chemical Engineering Research and Design, 2021, pp. 54-68.
(Continued)

*Primary Examiner* — Kathryn Elizabeth Limbaugh
(74) *Attorney, Agent, or Firm* — KILE PARK REED & HOUTTEMAN PLLC

(57) ABSTRACT

Provided are nanoparticles for sensing phosphate, a method for manufacturing the same, and a membrane for sensing phosphate including the same. The nanoparticles for sensing phosphate include a coordination polymer in which lanthanide metal ions and ligands are coordinated, and a polymer.

16 Claims, 7 Drawing Sheets

(58) Field of Classification Search
CPC ... G01N 2021/6432; G01N 2021/6439; G01N 2021/7786; G01N 31/22; B01L 3/5023; B01L 3/069; B01L 2300/069
See application file for complete search history.

(56) References Cited

U.S. PATENT DOCUMENTS

| | | |
|---|---|---|
| 10,156,558 B2 | 12/2018 | Harma |
| 2003/0138876 A1 | 7/2003 | Ponce et al. |
| 2009/0082368 A1* | 3/2009 | Vohra ................ A61P 1/00 514/257 |
| 2015/0047417 A1 | 2/2015 | Park et al. |
| 2021/0139390 A1 | 5/2021 | Fukubayashi et al. |

OTHER PUBLICATIONS

Sasaki et al: "Phosphate Anion Sensing Based on Preorganized Tripodal Ionophores", Analytical Sciences, vol. 17 Supplement, 2001, pp. i1659 to i1661.

Xiangyang Song et al., "Europium-based infinite coordination polymer nanospheres as an effective fluorescence probe for phosphate sensing", RSC Advances., 2017, 7, pp. 8661-8669.

Do Yeob Kim et al., "Reusable and pH-Stable Luminescent Sensors for Highly Selective Detection of Phosphate", Polymers 2022, 14, 190.

Donggyu Kim et al., "Membrane containing Eu-Coordination Polymer Nanoparticles for highly selective detection of phosphate ions", 128th General Meeting of the Korean Chemical Society.

\* cited by examiner

NANOPARTICLES FOR SENSING PHOSPHATE, METHOD FOR MANUFACTURING THE SAME, AND MEMBRANE FOR SENSING PHOSPHATE INCLUDING THE SAME

CROSS-REFERENCE TO RELATED APPLICATION

This U.S. non-provisional patent application claims priority under 35 U.S.C. § 119 of Korean Patent Application No. 10-2022-0007806, filed on Jan. 19, 2022, the entire contents of which are hereby incorporated by reference.

BACKGROUND

The present disclosure herein relates to nanoparticles for sensing phosphate which may sense phosphate in real time, a method for manufacturing the same, and a membrane for sensing phosphate including the same.

Phosphorus present in water is one of the essential nutrients for the survival of aquatic organisms, and sometimes causes an algal bloom depending on the amount of phosphorus present, which threatens the survival of other aquatic organisms, or acts as a pollution source for aquatic ecosystems. Accordingly, the Ministry of Environment in Korea has made and operated a standard for quantitatively analyzing phosphorus-related items such as total phosphorus, dissolved total phosphorus, and orthophosphate in the Method of Official Test for Water Pollution in order to manage the water environment. Thus, it is needed to monitor the phosphorus (P) component in order to prevent water pollution as well as to fully understand the aquatic ecosystems. However, there are chemical additives for oxidation/reduction reactions and chemical processes for smooth chemical reactions in the quantitative analysis of phosphorus-related items presented by water environment management, and thus there is a limitation in monitoring phosphorus components without immediate and additional processing. As an example, to analyze total phosphorus, according to the Method of Official Test for Water Pollution, the concentration of phosphorus has been determined through chemical reactions such as addition of external additional chemicals and heating or ultraviolet irradiation for at least 30 minutes. In this way, it is impossible to sense the concentration of phosphorus in real time, and it is difficult to determine the appropriate enforcement of measures for preventing water pollution through immediate monitoring.

Colorimetry or electrochemical analysis is generally provided as a method for sensing phosphate in water. The colorimetry is a method used in the Method of Official Test for Water Pollution, and requires additional chemical additives and high-temperature/high-pressure chemical reactions and the resultant reaction time. Therefore, it is not suitable for a direct reading sensor method. In the electrochemical analysis, an ion-selective membrane is used to sense a change in membrane potential according to the presence of phosphate, thereby analyzing phosphate without additional chemical additives. However, it is difficult to use the electrochemical analysis in the field because the selectivity to other ions is not good, and durability cannot be secured due to deformation of a polymer sensing film, and thus the electrochemical analysis is utilized for quantitative analysis of phosphate at the laboratory level.

SUMMARY

The present disclosure provides nanoparticles for sensing phosphate including lanthanide metal ions, a method for manufacturing the same, and a membrane for sensing phosphate including the same.

The purpose of the present disclosure is not limited to the aforementioned, but other purposes not described herein will be clearly understood by those skilled in the art from descriptions below.

An embodiment of the inventive concept provides nanoparticles for sensing phosphate, the nanoparticles including a polymer, and a coordination polymer in which lanthanide metal ions and ligands are coordinated.

In an embodiment of the inventive concept, a method for sensing phosphate includes: reacting nanoparticles with phosphate; and measuring a decrease in luminescence intensity of the nanoparticles. The nanoparticles include a coordination polymer in which lanthanide metal ions and ligands are coordinated, and a polymer.

In an embodiment of the inventive concept, a method for manufacturing nanoparticles for sensing phosphate includes: adding lanthanide metal ions, ligands, and polymers into an organic solvent to form a mixed solution; heating and pressurizing the mixed solution; and performing centrifugation on the mixed solution to obtain nanoparticles for sensing phosphate, wherein the nanoparticles for sensing phosphate include a coordination polymer in which the lanthanide metal ions and the ligands are coordinated, and a polymer.

In an embodiment of the inventive concept, a membrane for sensing phosphate includes a porous membrane, and nanoparticles for sensing phosphate which are fixed on the porous membrane, wherein the nanoparticles for sensing phosphate include a coordination polymer in which lanthanide metal ions and ligands are coordinated, and a polymer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
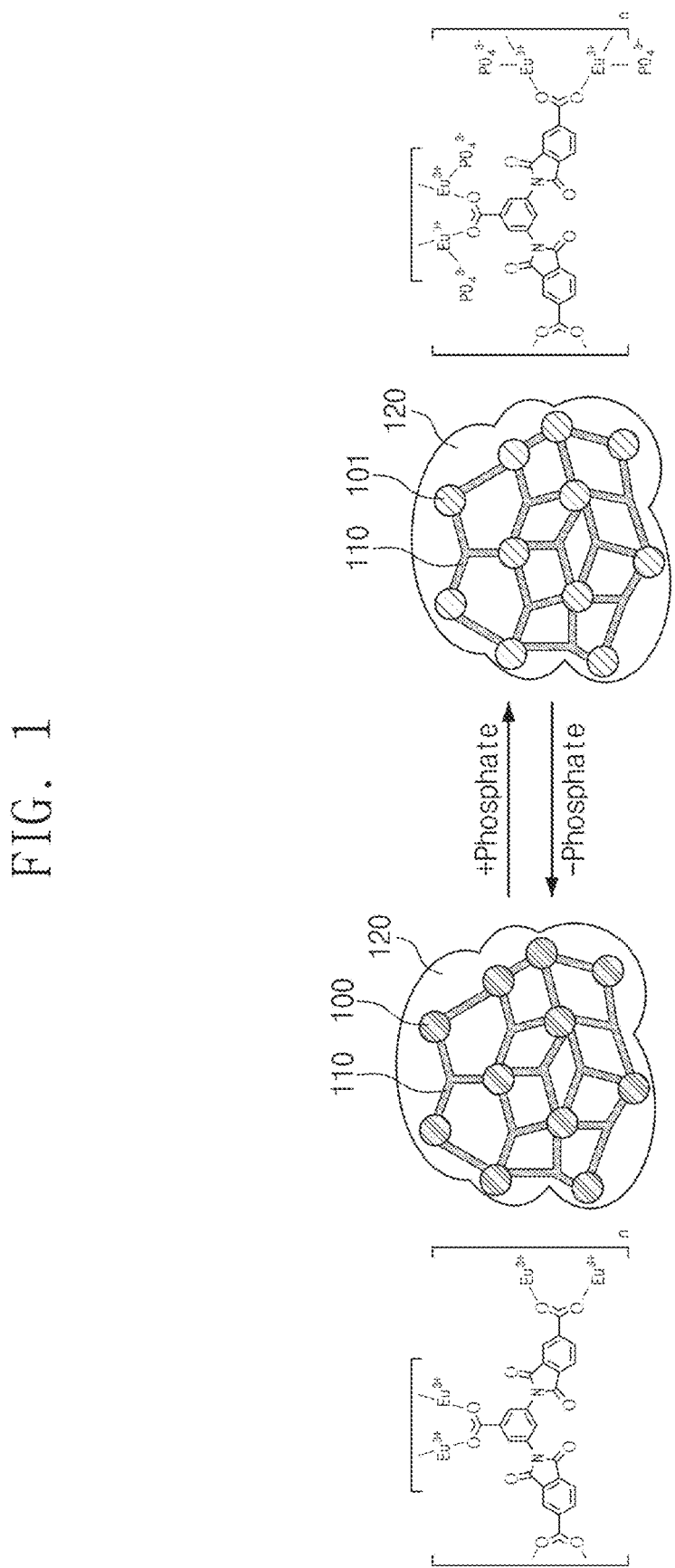
FIG. 1 is a schematic view illustrating a structure of nanoparticles for sensing phosphate and a structure of nanoparticles reacted with phosphate according to the inventive concept.

The advantages and the features of the inventive concept, and methods for attaining them will be described in example embodiments below with reference to the accompanying drawings. The inventive concept may, however, be embodied in different forms and should not be construed as limited to the embodiments set forth herein. Rather, these embodiments are provided so that this description will be thorough and complete, and will fully convey the scope of the present inventive concept to those skilled in the art. The inventive concept is defined by the scope of the claims attached herein only. Like reference numerals refer to like elements throughout.

In this specification, the terms are used only for explaining embodiments while not limiting the present disclosure. In the specification, the terms of a singular form may include plural forms unless referred to the contrary. It will be understood that the terms 'comprises' and/or 'comprising', when used in this specification, specify the presence of stated components, steps, operations and/or elements, but do not preclude the presence or addition of one or more other components, steps, operations and/or elements.

It will be understood that when a film (or layer) is referred to as being 'on' another film (or layer) or substrate, it can be directly on the another film (or layer) or substrate, or intervening films (or layers) may also be present therebetween.

In addition, embodiments described herein will be explained with reference to cross-sectional views and/or plan views that are ideal example views of the inventive concept.

In the drawings, the thicknesses of layers and regions may be exaggerated for effective explanation of technical contents. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the present inventive concept.

Unless otherwise defined, all terms used herein have the same meaning as commonly understood by one of ordinary skill in the art to which this inventive concept belongs.

FIG. 1 is a schematic view illustrating a structure of nanoparticles for sensing phosphate and a structure of nanoparticles reacted with phosphate according to the inventive concept.

Referring to FIG. 1, the nanoparticles for sensing phosphate according to the inventive concept may include a coordination polymer in which lanthanide metal ions 100 and ligands 110 are coordinated. The lanthanide metal ions 100 may include, for example, europium ($Eu^{3+}$). The ligands 110 may include tripod ligands. The tripod ligands may be bonded to multiple metal ions via tridentate bonding, and thus have high chemical stability in a wide range of pH. As an example, although one coordination bond is weakened by the bonding with phosphate, the remaining two coordination bonds are maintained and thus high stability may be exhibited. The ligands 110 may include, for example, 2,2'-(5-carboxy-1,3-phenylene)bis(1,3-dioxoisoindoline-5-carboxylic acid). The nanoparticles for sensing phosphate according to the inventive concept may further include a polymer 120. The polymer 120 may include, for example, polyvinylpyrrolidone (PVP). The polymer 120 may be a capping polymer. For example, the polymer 120 may surround the nanoparticles for sensing phosphate including the lanthanide metal ions 100 and the ligands 110. The nanoparticles for sensing phosphate may be, for example, a metal complex form or a composite form of a coordination polymer (as an example, subnanoparticles) and a polymer. The nanoparticles for sensing phosphate may have, for example, a diameter of about 50 nm to about 150 nm.

As illustrated in FIG. 1, due to the lanthanide metal ions 100 having luminescence characteristics, luminescent coordination polymer nanoparticles (CPPs) for sensing phosphate may be provided. However, when phosphate is added, the lanthanide metal ions 100 react with phosphate, luminescence characteristics may be attenuated, and quenched lanthanide metal ions 101 may be provided. That is, luminescent CPPs for sensing phosphate react with phosphate to be transformed into quenched CPPs for sensing phosphate. In this case, the phosphate may include, for example, at least one of inorganophosphate, organophosphate, or organophosphonate.

Figure 2:
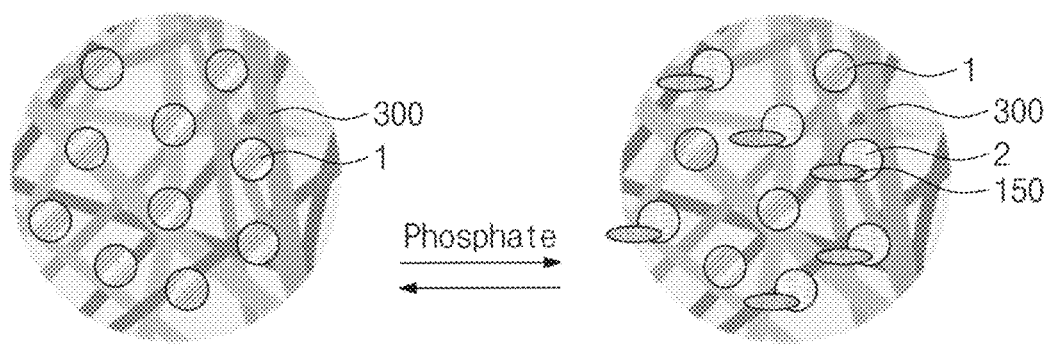
FIG. 2 is a schematic view illustrating a mechanism for sensing phosphate by using nanoparticles for sensing phosphate fixed on a membrane according to the inventive concept.

FIG. 2 is a schematic view illustrating a mechanism for sensing phosphate by using nanoparticles for sensing phosphate fixed on a membrane according to the inventive concept. FIG. 2 illustrates nanoparticles 1 for sensing phosphate, which are not reacted with phosphates and nanoparticles 2 for sensing phosphate, which are reacted with phosphates 150. Referring to FIG. 2, the phosphate 150 may include, for example, at least one of inorganophosphate, organophosphate, or organophosphonate. The nanoparticles 1 for sensing phosphate, which are not reacted with phosphates, may be fixed on a membrane 300.

In this case, the nanoparticles 1 for sensing phosphate, which are not reacted with phosphates, may have luminescence characteristics. More specifically, when irradiated with ultraviolet rays, the luminescence characteristics may be exhibited by the lanthanide metal ions in the nanoparticles for sensing phosphate. When the phosphates 150 are added, the nanoparticles 2 for sensing phosphate, which are reacted with the phosphates 150, may have attenuated luminescence characteristics, and quenched luminescence characteristics. More specifically, as the nanoparticles for sensing phosphate react with the phosphates 150, the luminescence characteristics of the lanthanide metal ions in the nanoparticles 2 for sensing phosphate, which are reacted with the phosphates 150, may be attenuated and thus the quenched luminescence characteristics may be exhibited. Accordingly, by measuring the decreased luminescence intensity of the nanoparticles for sensing phosphate of the inventive concept according to the addition of phosphate, the concentration of phosphate may be measured in real time and with high sensitivity. The membrane 300 may be, for example, a filter membrane. The membrane 300 may include, for example, a porous membrane. The membrane 300 may include, for example, at least one of PVC, glass microfiber, or nylon. In some embodiments, unlike the conformation illustrated, the nanoparticles for sensing phosphate may be present in a state dispersed in an aqueous solution.

A method for manufacturing nanoparticles for sensing phosphate according to the inventive concept may include adding lanthanide metal ions, ligands, and polymers into an organic solvent to form a mixed solution, heating and pressurizing the mixed solution, and performing centrifugation on the mixed solution to obtain nanoparticles for sensing phosphate. The lanthanide metal ions may include, for example, europium ($Eu^{3+}$). The ligands may include, for example, 2,2'-(5-carboxy-1,3-phenylene)bis(1,3-dioxoisoindoline-5-carboxylic acid). The polymer may include, for example, polyvinylpyrrolidone (PVP). The organic solvent may include dimethylformaldehyde and ethanol. The organic solvent may further include sulfuric acid. The heating may be performed at about 100° C. to about 200° C. The heating may be performed, for example, at about 150° C. The performing of the centrifugation on the mixed solution may include adding dimethylformaldehyde (DMF) into the mixed solution, applying ultrasonic waves to the mixed solution to be dispersed, and removing impurities through the centrifugation.

EXAMPLE 1

$EuCl_3 \cdot 6H_2O$ (235 mg, 0.64 mmol, 5.3 eq) and tripod ligands (60 mg, 0.12 mmol, 1 eq) were dissolved in a mixed solvent of 32 mL of dimethylformaldehyde (DMF) and 19.2 mL of ethanol. Here, (2,2'-(5-carboxy-1,3-phenylene)bis(1,3-dioxoisoindoline-5-carboxylic acid) was used as the tripod ligand. Polyvinylpyrrolidone (PVP, 1600 mg), which acts as an additional ligand, was added to the mixed solvent, and mixed to prepare a mixed solution. Concentrated sulfuric acid (3.3 µL) was added to the mixed solution, and then fully dissolved for about 30 minutes while ultrasonic waves are applied thereto. The mixed solution was put into a high pressure reactor equipped with a teflon container, and the reactor was sealed, and then the mixed solution was reacted at about 150° C. for about 12 hours. Then, the mixed solution was slowly cooled to room temperature over about 6 hours. Accordingly, the formed colloidal nanoparticles were centrifuged and the supernatant was discarded. Dimethyl formaldehyde (DMF) was newly added to the separated nanoparticles, then dispersed by applying ultrasonic waves, and centrifuged to remove impurities, and this process was repeated three times. Finally, the nanoparticles were washed once with ethanol. The nanoparticles were dried at about 70° C. for about 3 hours to obtain lanthanide coordination polymer nanoparticles that are nanoparticles for sensing phosphate in a pinky-white solid form.

Experimental Example 1

Figure 3A:
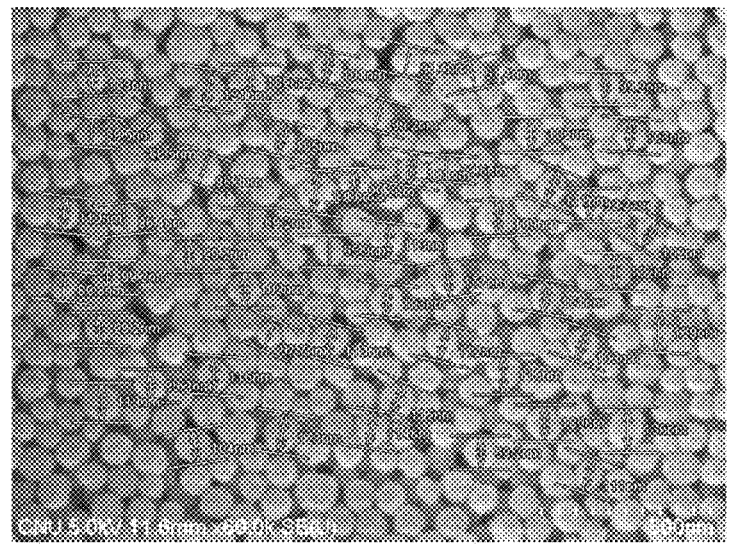
FIG. 3A shows a scanning electron microscope photograph of the nanoparticles for sensing phosphate manufactured according to Example 1.
Figure 3B:
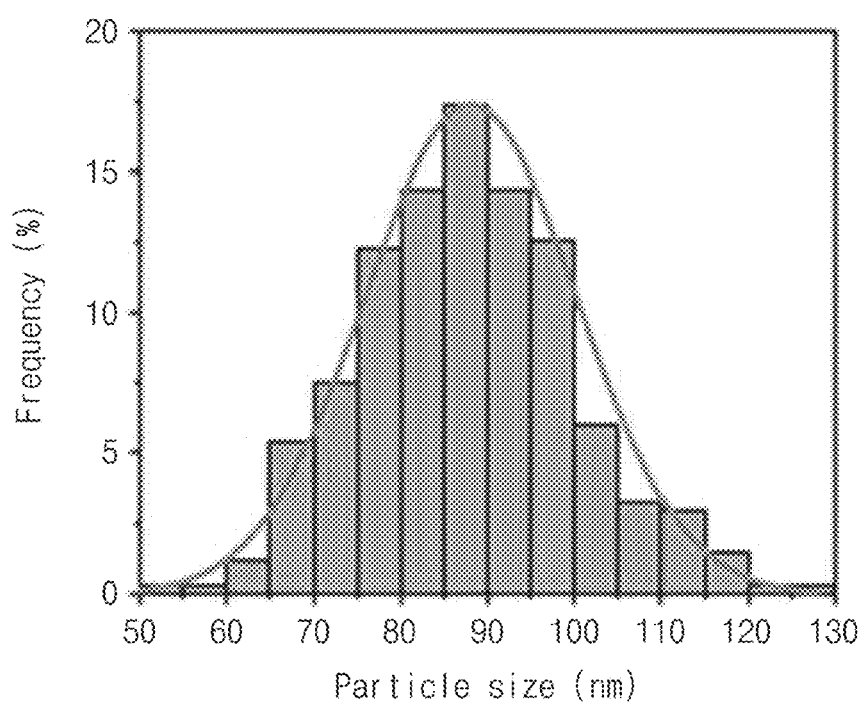
FIG. 3B shows a particle size distribution graph of the nanoparticles for sensing phosphate manufactured according to Example 1.

FIG. 3A shows a scanning electron microscope photograph of the nanoparticles for sensing phosphate manufactured according to Example 1. FIG. 3B shows a particle size distribution graph of the nanoparticles for sensing phosphate manufactured according to Example 1.

Referring to FIGS. 3A and 3B, it may be confirmed that the obtained nanoparticles for sensing phosphate have a spherical shape. In addition, when the size of 334 obtained nanoparticles for sensing phosphate was analyzed, it may be confirmed that the nanoparticles have a size of about 88.1±12.2 nm. The size and/or shape of the produced nanoparticles may vary depending on the composition ratio of used Eu ions, tripod ligands, and polyvinylpyrrolidone (PVP), and/or a solvent. The nanoparticles for sensing phosphate according to the inventive concept may have a nanosized-diameter, and a uniform size within about 100 nm. Accordingly, the nanoparticles for sensing phosphate according to the inventive concept have an advantage of being uniformly dispersed in an aqueous solution without sedimentation by gravity. In addition, when the nanoparticles for sensing phosphate according to the inventive concept is impregnated into the membrane, there is an advantage in that the nanoparticles are effectively fixed on a porous structure present in the membrane without additional adhesive.

Experimental Example 2

Figure 4A:
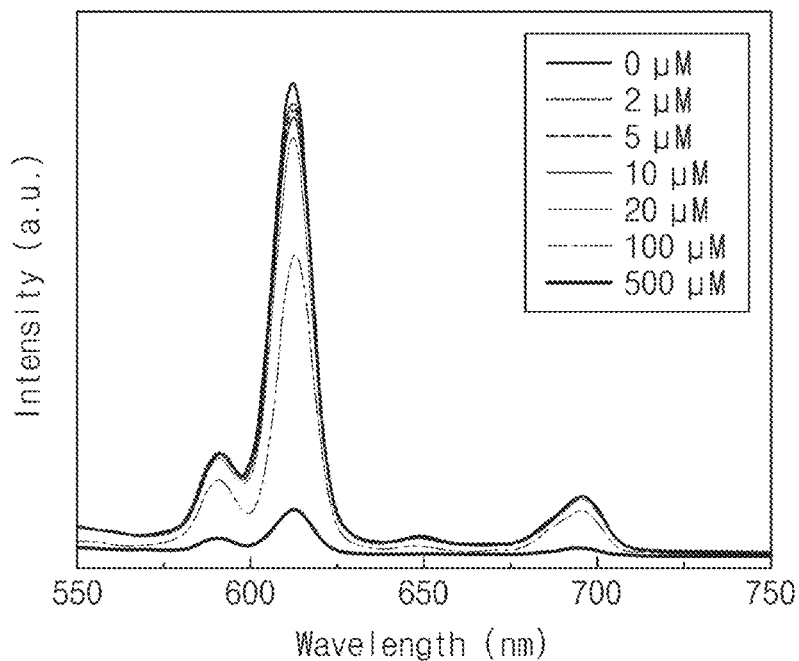
FIG. 4A is a graph showing luminescence characteristics when phosphate having various concentrations is sensed in a state in which the nanoparticles for sensing phosphate manufactured according to Example 1 are dispersed in a solution.
Figure 4B:
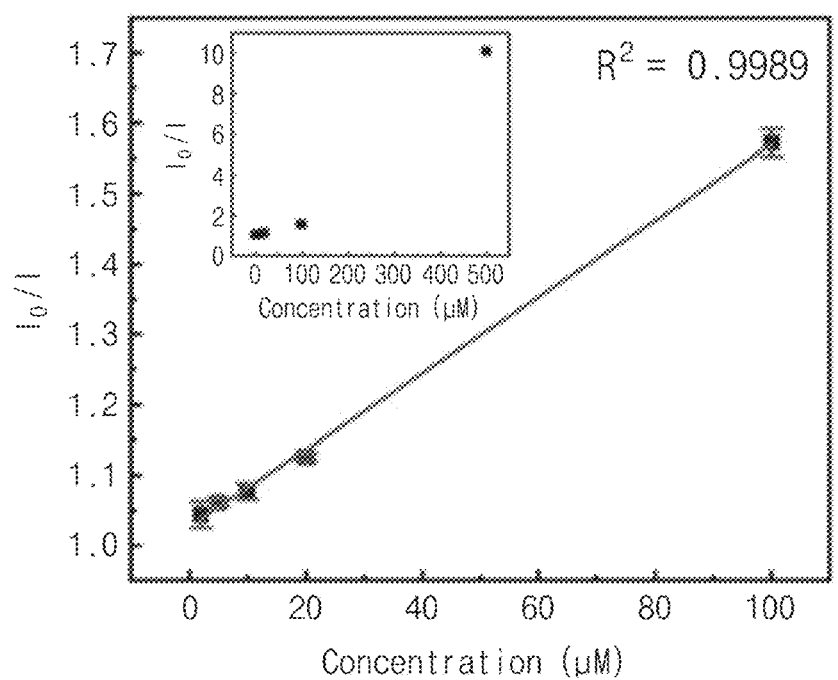
FIG. 4B is a graph showing a relative change ($I_0/I$) of luminescence intensity when the nanoparticles for sensing phosphate manufactured according to Example 1 sense phosphate at various concentrations.

FIG. 4A is a graph showing luminescence characteristics when phosphate having various concentrations is sensed in a state in which the nanoparticles for sensing phosphate manufactured according to Example 1 are dispersed in a solution. FIG. 4B is a graph showing a relative change ($I_0/I$) of luminescence intensity when the nanoparticles for sensing phosphate manufactured according to Example 1 sense phosphate at various concentrations.

The nanoparticles for sensing phosphate were irradiated with 260 nm-ultraviolet rays and excited, and the luminescence characteristics were observed in a region of 615 nm-visible light. Referring to FIGS. 4A and 4B, it may be confirmed that phosphates may be sensed at various concentrations from about 2 µM to about 500 µM. More specifically, it may be confirmed that as the phosphate concentration increases, the reduction rate of the luminescence intensity increases. In particular, it may be confirmed that when the phosphate having a concentration of about 500 µM was sensed, the luminescence characteristics were attenuated by about 90% relative to initial luminescence characteristics, and 10% luminescence characteristics are exhibited.

To repeatedly utilize nanoparticles for sensing phosphate according to the inventive concept in phosphate concentration analysis, the nanoparticles for sensing phosphate were fixed on a membrane. In this case, the membrane may be a filter membrane as an example, and may include, for example, PVC, glass microfiber, and/or nylon material. The nanoparticles for sensing phosphate may be adsorbed on the surface of the membrane. For example, pores of the membrane may have a size of several hundreds nm to several scores µm.

The nanoparticles for sensing phosphate having a particle size of about 50 nm to about 150 nm manufactured according to Example 1 were used to prepare nanoparticle dispersion for sensing phosphate at the concentration of about 0.01 wt % to about 10 wt %. In this case, as the solvent of the nanoparticle dispersion for sensing phosphate, water, a volatile organic solvent, or the like may be used, for example. The nanoparticle dispersion for sensing phosphate may be dropped on the surface of the membrane, or the membrane may be immersed into the nanoparticle dispersion for sensing phosphate. Thereafter, the membrane may be dried by using a heater or according to a natural drying method. After the membrane was dried, in order to remove the nanoparticles for sensing phosphate which are not adsorbed on the surface of the membrane, the membrane may be washed several times by using water or a volatile organic solvent, and then redried.

Experimental Example 3

Figure 5A:
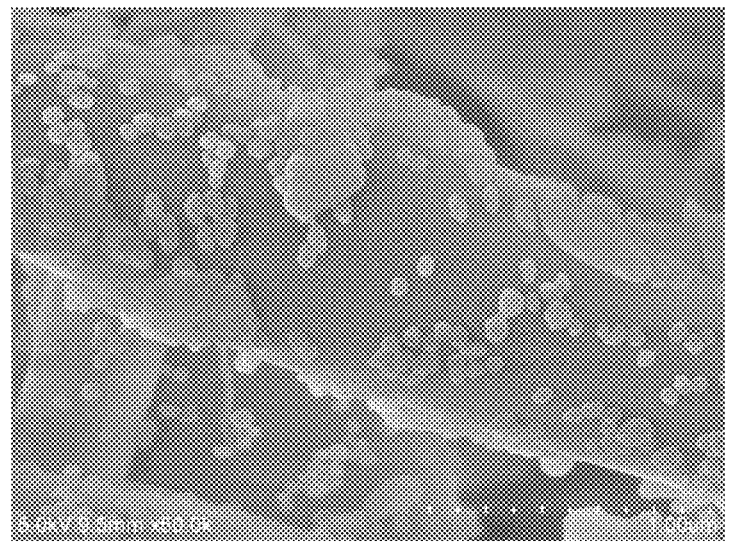
FIG. 5A shows a scanning electron microscope photograph of the nanoparticles for sensing phosphate fixed on a membrane according to Example 2.
Figure 5B:
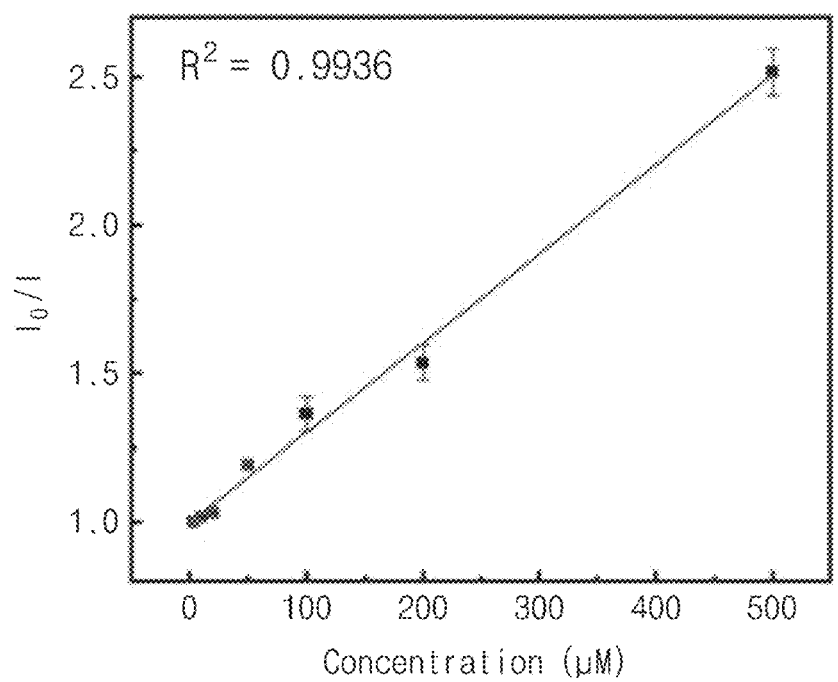
FIG. 5B is a graph showing a relative change ($I_0/I$) of luminescence intensity when the nanoparticles for sensing phosphate fixed on the membrane according to Example 2 sense phosphate at various concentrations.

FIG. 5A shows a scanning electron microscope photograph of the nanoparticles for sensing phosphate fixed on a membrane according to Example 2. FIG. 5B is a graph showing a relative change ($I_0/I$) of luminescence intensity when the nanoparticles for sensing phosphate fixed on the membrane according to Example 2 sense phosphate at various concentrations.

Referring to FIG. 5A, it may be confirmed that the nanoparticles for sensing phosphate are fixed on the membrane through a scanning electron microscope. By using this, an experiment for sensing a phosphate solution with a concentration of about 500 μM or less was conducted. As a result, referring to FIG. 5B, it may be seen that a luminescence signal is attenuated by 40% at a concentration of about 500 μM. It may be confirmed that the nanoparticles for sensing phosphate effectively sense phosphate even when they are fixed on the membrane. As a result of analyzing the lower limit concentration sensed from the correlation between the phosphate concentration and the relative change in the luminescence intensity ($I_0/I$), it may be confirmed that the sensed lower limit (3 sigma/slope, sigma=$I_0/I$ standard deviation, slope=$I_0/I$ vs linear slope of the phosphate concentration graph) of the nanoparticles for sensing phosphate fixed on the membrane is about 1.52 μM.

Figure 6A:
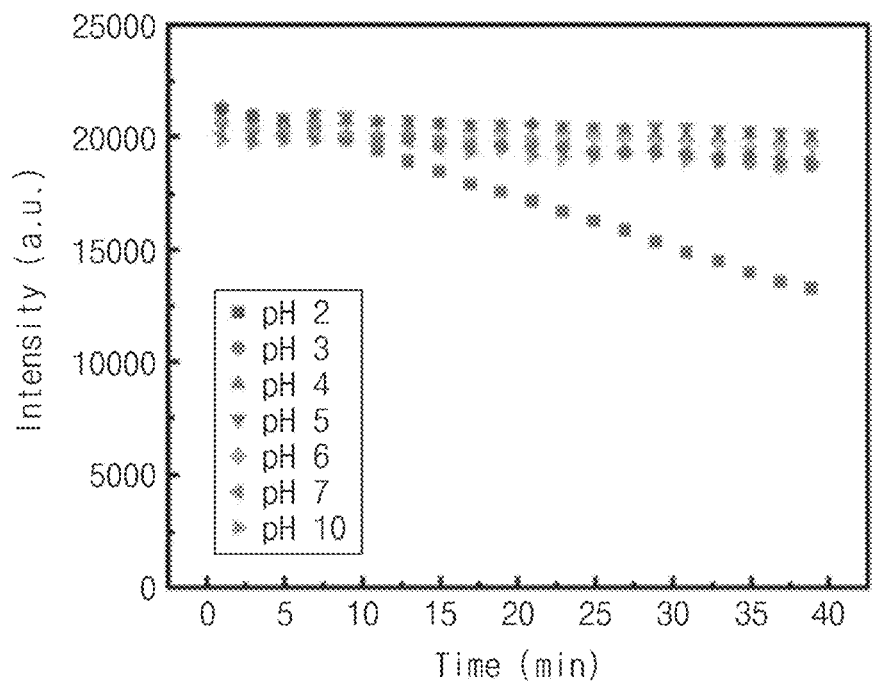
FIG. 6A is a graph showing signal stability according to various acidity (pH) of the nanoparticles for sensing phosphate fixed on the membrane according to Example 2.
Figure 6B:
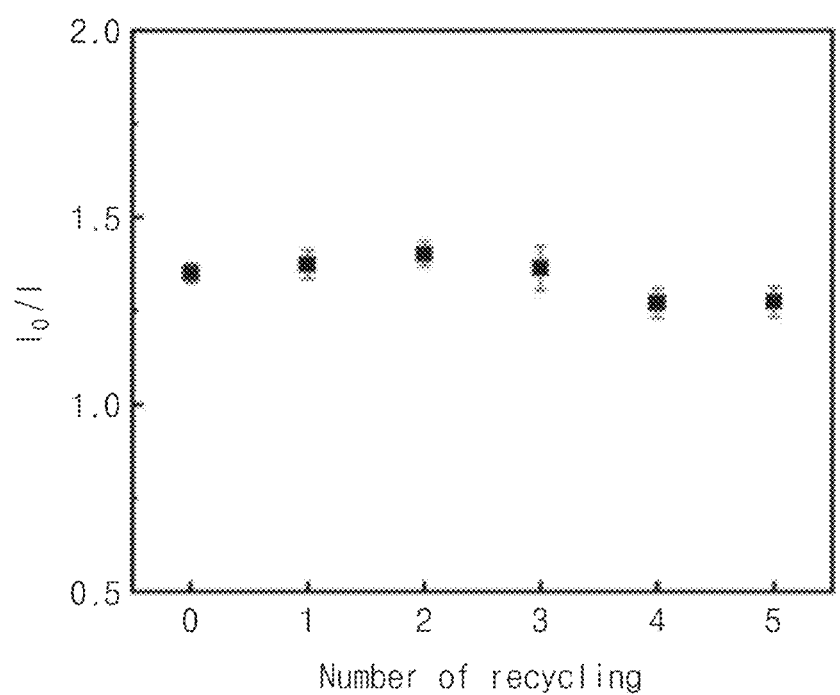
FIG. 6B is a graph showing a relative change ($I_0/I$) of luminescence intensity according to continuous measurement of the nanoparticles for sensing phosphate fixed on the membrane according to Example 2.

FIG. 6A is a graph showing signal stability according to various acidity (pH) of the nanoparticles for sensing phosphate fixed on the membrane according to Example 2. FIG. 6B is a graph showing a relative change ($I_0/I$) of luminescence intensity according to continuous measurement of the nanoparticles for sensing phosphate fixed on the membrane according to Example 2.

Referring to FIG. 6A, when the nanoparticles for sensing phosphate fixed on the membrane were immersed in an aqueous solution having various acidity of about pH 2 to about pH 10 for 40 minutes, a luminescence signal was examined. It may be confirmed that although the luminescence signal is changed in a certain amount (about 25%) at about pH 2, the luminescence signal is constantly maintained for 40 minutes under other acidity conditions (about pH 3 to about pH 10). Based on this, it may be confirmed that the nanoparticles for sensing phosphate according to the inventive concept may be used to sense phosphate in various environments. Referring to FIG. 6B, it may be confirmed that the nanoparticles for sensing phosphate according to the inventive concept are fixed on the membrane even during measurement, and thus, the substantially same quenching signal may be exhibited as the same concentration of phosphate is sensed even during 5 consecutive measurements.

Figure 7:
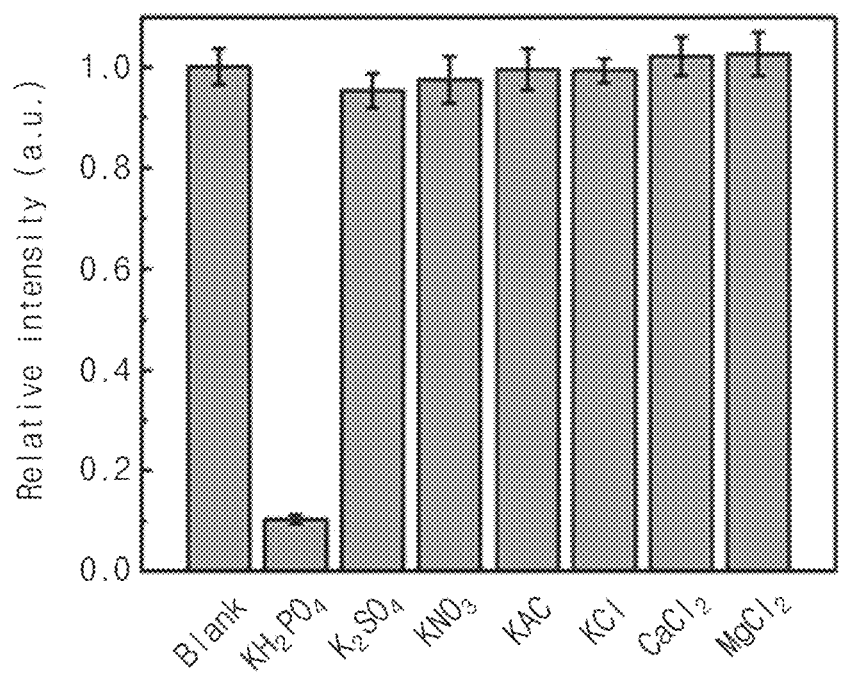
FIG. 7 is a graph showing signal selectivity of the nanoparticles for sensing phosphate fixed on the membrane according to Example 2 with respect to other ions as compared with phosphate.

FIG. 7 is a graph showing signal selectivity of the nanoparticles for sensing phosphate fixed on the membrane according to Example 2 with respect to other ions as compared with phosphate. In the field, various ions exist in addition to phosphate. Referring to FIG. 7, it may be seen that in a solution in which sulfate, nitrate, acetate, and chlorine ions are present at a certain concentration, the luminescence characteristics of the nanoparticles for sensing phosphate are not consistently attenuated, and only in the phosphate solution, the luminescence characteristics of the nanoparticles for sensing phosphate are attenuated. Accordingly, it may be confirmed that the nanoparticles for sensing phosphate according to the inventive concept exhibit phosphate selectivity.

The nanoparticles for sensing phosphate according to the inventive concept may include lanthanide metal ions. When the nanoparticles for sensing phosphate react with phosphate, luminescence characteristics may be attenuated and quenching characteristics may be exhibited. Accordingly, by measuring the decreased luminescence intensity of the nanoparticles for sensing phosphate, the concentration of phosphate may be measured in real time and with high sensitivity.

Also, additional oxidation/reduction agents and color fixing agents are not required, and high-temperature heat treatment is not accompanied, and thus phosphate in water may be sensed in real time. In addition, the nanoparticles are not used just one time, and installed in the field, and thus continuous measurement is possible in an unmanned operable form. Accordingly, the nanoparticles for sensing phosphate having improved reliability in the field may be provided.

Although the embodiments of the inventive concept have been described with reference to the accompanying drawings, those with ordinary skill in the technical field to which the inventive concept pertains will understood that the present disclosure can be carried out in other specific forms without changing the technical idea or essential features. Therefore, the above-disclosed embodiments are to be considered in all aspects as illustrative and not restrictive.

What is claimed is:

1. A method for sensing phosphate, the method comprising: reacting nanoparticles with phosphate; and measuring a decrease in luminescence intensity of the nanoparticles, wherein the nanoparticles comprises: a coordination polymer in which lanthanide metal ions and ligands are coordinated, wherein the ligands comprise 2,2'-(5-carboxy-1,3-phenylene)bis(1,3-dioxoisoindoline-5-carboxylic acid); and a polymer.

2. The method of claim 1, wherein the lanthanide metal ions comprise europium ($Eu^{3+}$).

3. The method of claim 1, wherein the ligands comprise tripod ligands.

4. The method of claim 1, wherein the polymer comprises polyvinylpyrrolidone (PVP).

5. The method of claim 1, wherein the nanoparticles for sensing phosphate have a diameter of about 50 nm to about 150 nm.

6. A method for manufacturing nanoparticles for sensing phosphate comprising: adding lanthanide metal ions, ligands, and polymers into an organic solvent to form a mixed solution; heating and pressurizing the mixed solution; and performing centrifugation on the mixed solution to obtain nanoparticles for sensing phosphate, wherein the nanoparticles for sensing phosphate comprise: a coordination polymer in which the lanthanide metal ions and the ligands are coordinated, wherein the ligands comprise 2,2'-(5-carboxy-1,3-phenylene)bis(1,3-dioxoisoindoline-5-carboxylic acid groups); and a polymer.

7. The method of claim 6, wherein the organic solvent comprises dimethylformaldehyde and ethanol.

8. The method of claim 7, wherein the organic solvent further comprises sulfuric acid.

9. The method of claim 6, wherein the heating is performed at about 100° C. to about 200° C.

10. The method of claim 6, wherein the performing of the centrifugation on the mixed solution comprises:
   adding dimethylformaldehyde (DMF) into the mixed solution,
   applying ultrasonic waves to the mixed solution to be dispersed; and
   removing impurities through the centrifugation.

11. The method of claim 6, wherein the nanoparticles for sensing phosphate have a diameter of about 50 nm to about 150 nm.

12. The method of claim 2, wherein the lanthanide metal ions comprise europium ($Eu^{3+}$).

13. The method of claim 6, wherein the polymer comprises polyvinylpyrrolidone (PVP).

14. A membrane for sensing phosphate comprising: a porous membrane; and nanoparticles for sensing phosphate which are fixed on the porous membrane, wherein the nanoparticles for sensing phosphate comprises: a coordination polymer in which lanthanide metal ions and ligands are coordinated, wherein the lanthanide metal ions comprise europium ($Eu^{3+}$), and the ligands comprise 2,2'-(5-carboxy-1,3-phenylene) bi s (1,3-dioxoisoindoline-5-carboxylic acid); and a polymer, wherein the polymer comprises polyvinylpyrrolidone (PVP).

15. The membrane of claim 14, wherein the porous membrane comprises at least one of PVC, glass microfiber, or nylon.

16. The membrane of claim 14, wherein the nanoparticles for sensing phosphate have a diameter of about 50 nm to about 150 nm.

* * * * *